US012023134B2

(12) United States Patent
Hocking et al.

(10) Patent No.: US 12,023,134 B2
(45) Date of Patent: Jul. 2, 2024

(54) NON-INVASIVE VENOUS WAVEFORM ANALYSIS FOR EVALUATING A SUBJECT

(71) Applicant: Vanderbilt University, Nashville, TN (US)

(72) Inventors: Kyle M. Hocking, Nashville, TN (US); Colleen M. Brophy, Nashville, TN (US); Susan S. Eagle, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 347 days.

(21) Appl. No.: 17/273,809

(22) PCT Filed: Sep. 5, 2019

(86) PCT No.: PCT/US2019/049781
§ 371 (c)(1),
(2) Date: Mar. 5, 2021

(87) PCT Pub. No.: WO2020/051354
PCT Pub. Date: Mar. 12, 2020

(65) Prior Publication Data
US 2021/0315465 A1 Oct. 14, 2021

Related U.S. Application Data

(60) Provisional application No. 62/727,735, filed on Sep. 6, 2018.

(51) Int. Cl.
*A61B 5/0205* (2006.01)
*A61B 5/00* (2006.01)
(52) U.S. Cl.
CPC ............ *A61B 5/0205* (2013.01); *A61B 5/725* (2013.01); *A61B 5/7257* (2013.01)

(58) Field of Classification Search
CPC ...... A61B 5/0205; A61B 5/725; A61B 5/7257
(Continued)

(56) References Cited

U.S. PATENT DOCUMENTS

2006/0178588 A1* 8/2006 Brody ................ A61B 5/02455
600/513
2010/0152600 A1* 6/2010 Droitcour ............. A61B 5/1113
600/534

(Continued)

FOREIGN PATENT DOCUMENTS

JP        H06292721 A      10/1994
JP        2015-171394 A    10/2015
(Continued)

OTHER PUBLICATIONS

Office Action for Japanese Patent Application No. 2021-512566, mailed Apr. 14, 2023.
(Continued)

*Primary Examiner* — Carl H Layno
*Assistant Examiner* — Michael J Lau
(74) *Attorney, Agent, or Firm* — McDonnell Boehnen Hulbert & Berghoff LLP

(57) ABSTRACT

An example method includes (a) generating, via a sensor of a computing device, a signal representing vibrations originating from a blood vessel of a subject, where the vibrations are indicative of heart beats and/or respirations of the subject; (b) using the signal to determine first times elapsed between respective pairs of consecutive heartbeats indicated by the vibrations and/or second times elapsed between respective pairs of consecutive respirations indicated by the vibrations; and (c) using the determined first times elapsed to determine a heart rate variability of the subject and/or the determined second times elapsed to determine a respiration rate variability of the subject.

20 Claims, 16 Drawing Sheets

(58) Field of Classification Search
USPC .......................................................... 600/301
See application file for complete search history.

(56) References Cited

U.S. PATENT DOCUMENTS

| | | | | |
|---|---|---|---|---|
| 2010/0268104 | A1* | 10/2010 | Lee ...................... | A61B 5/7253 600/519 |
| 2011/0112419 | A1* | 5/2011 | Bjorling ............... | A61B 5/0809 600/509 |
| 2011/0251493 | A1* | 10/2011 | Poh ..................... | G06F 18/2134 382/128 |
| 2013/0281795 | A1* | 10/2013 | Varadan .................. | A61B 7/04 977/762 |
| 2014/0128753 | A1* | 5/2014 | Luna .................. | A61B 5/02438 600/528 |
| 2017/0071546 | A1* | 3/2017 | Jain ...................... | A61B 5/0533 |
| 2017/0128020 | A1* | 5/2017 | Olivier ................... | A61B 5/721 |
| 2017/0181691 | A1* | 6/2017 | Olivier ................ | A61B 5/4812 |
| 2017/0332919 | A1* | 11/2017 | Eagle .................. | A61B 5/7257 |
| 2018/0103913 | A1* | 4/2018 | Tzvieli ................. | G06V 10/462 |
| 2018/0235540 | A1* | 8/2018 | Kirszenblat .......... | A61B 5/6803 |

FOREIGN PATENT DOCUMENTS

| | | |
|---|---|---|
| WO | 2016/077765 A1 | 5/2016 |
| WO | WO2017141976 A1 | 2/2018 |
| WO | 2018/073939 A1 | 6/2019 |

OTHER PUBLICATIONS

Combined PCT International Search Report and Written Opinion, PCT App. No. PCT/US2019/049781, mailed Dec. 12, 2019, 17 pages.

Lázaro, Jesús, Eduardo Gil, José María Vergara, and Pablo Laguna. "Pulse rate variability analysis for discrimination of sleep-apnea-related decreases in the amplitude fluctuations of pulse photoplethysmographic signal in children." IEEE journal of biomedical and health informatics 18, No. 1 (2013): 240-246.

Sileshi, Bantayehu, Kyle M. Hocking, Richard B. Boyer, Franz J. Baudenbacher, Kelly L. Kohurst, Colleen M. Brophy, and Susan Eagle. "Peripheral venous waveform analysis for detecting early hemorrhage: a pilot study." Intensive care medicine 41, No. 6 (2015): 1147-1148.

Hernando, David, Reid McCallister, Jesús Lázaro, Kyle Hocking, Eduardo Gil, Bret Alvis, Pablo Laguna, Colleen Brophy, and Raquel Bailón. "Validity of venous waveform signal for heart rate variability monitoring." In 2018 Computing in Cardiology Conference (CinC), vol. 45, pp. 1-4. IEEE, 2018.

Hernando, Alberto, Jesus Lazaro, Eduardo Gil, Adriana Arza, Jorge Mario Garzón, Raul Lopez-Anton, Concepcion de la Camara, Pablo Laguna, Jordi Aguiló, and Raquel Bailón. "Inclusion of respiratory frequency information in heart rate variability analysis for stress assessment." IEEE journal of biomedical and health informatics 20, No. 4 (2016): 1016-1025.

* cited by examiner

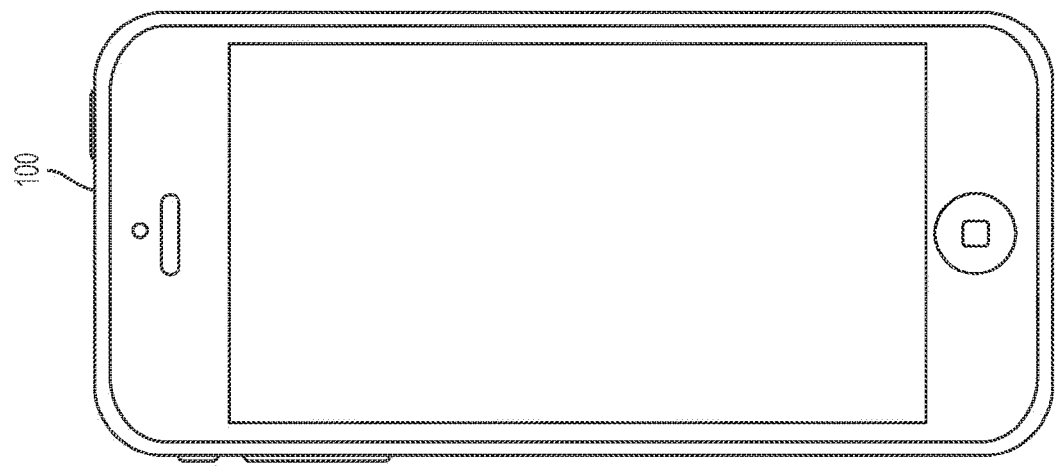
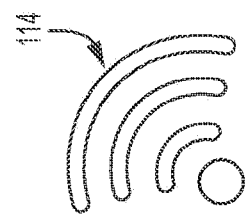
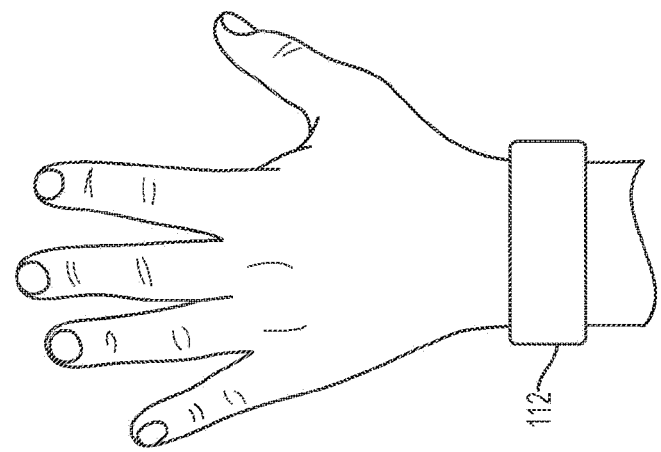
FIG. 2

NON-INVASIVE VENOUS WAVEFORM ANALYSIS FOR EVALUATING A SUBJECT

CROSS REFERENCE TO RELATED APPLICATION

This application is the US national phase under 35 U.S.C. § 371 of International Application No. PCT/US2019/049781, filed on Sep. 5, 2019, which claims priority to U.S. Provisional Patent Application No. 62/727,735, filed on Sep. 6, 2018, the contents of both of which are incorporated herein by reference in their entirety.

BACKGROUND

Unless otherwise indicated herein, the materials described in this section are not prior art to the claims in this application and are not admitted to be prior art by inclusion in this section.

Heart rate variability (HRV) can be used to assess autonomic nervous function of a subject. More specifically, HRV can be used to assess sympathetic (stress) and parasympathetic (anti-stress) responses of the nervous system. One difficulty that can be encountered is that the frequency ranges of the HRV that represent sympathetic and parasympathetic responses can overlap somewhat. HRV is typically derived from an electrocardiogram (ECG) but generally requires the use of contact electrodes, which can be inconvenient. As such, a need exists for more convenient means of assessing HRV and means for better distinguishing the frequency ranges of the HRV that correspond respectively to sympathetic and parasympathetic responses of the nervous system.

SUMMARY

In one example, a method includes (a) generating, via a sensor of a computing device, a signal representing vibrations originating from a blood vessel of a subject, where the vibrations are indicative of heart beats and/or respirations of the subject; (b) using the signal to determine first times elapsed between respective pairs of consecutive heart beats indicated by the vibrations and/or second times elapsed between respective pairs of consecutive respirations indicated by the vibrations; and (c) using the first determined times elapsed to determine a heart rate variability of the subject and/or the determined second times elapsed to determine a respiration rate variability of the subject.

In another example, a computing device includes one or more processors; a sensor; and a computer readable medium storing instructions that, when executed by the one or more processors, cause the computing device to perform functions. The functions include (a) generating, via the sensor, a signal representing vibrations originating from a blood vessel of a subject, where the vibrations are indicative of heart beats and/or respirations of the subject; (b) using the signal to determine first times elapsed between respective pairs of consecutive heart beats indicated by the vibrations and/or second times elapsed between respective pairs of consecutive respirations indicated by the vibrations; and (c) using the first determined times elapsed to determine a heart rate variability of the subject and/or the determined second times elapsed to determine a respiration rate variability of the subject.

In yet another example, a non-transitory computer readable medium stores instructions that, when executed by a computing device that includes a sensor, cause the computing device to perform functions. The functions include (a) generating, via the sensor, a signal representing vibrations originating from a blood vessel of a subject, where the vibrations are indicative of heart beats and/or respirations of the subject; (b) using the signal to determine first times elapsed between respective pairs of consecutive heart beats indicated by the vibrations and/or second times elapsed between respective pairs of consecutive respirations indicated by the vibrations; and (c) using the first determined times elapsed to determine a heart rate variability of the subject and/or the determined second times elapsed to determine a respiration rate variability of the subject.

These, as well as other aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrate the invention by way of example only and, as such, that numerous variations are possible.

BRIEF DESCRIPTION OF THE DRAWINGS

FIG. 2 depicts a computing device and a wireless sensor that is communicatively coupled to the computing device, according to an example embodiment.

DETAILED DESCRIPTION

As noted above, a need exists for more convenient means of assessing HRV and means for better distinguishing the frequency ranges of the HRV that correspond respectively to sympathetic and parasympathetic responses of the nervous system. Embodiments disclosed herein can help address these issues, as well as help in better obtaining a respiratory rate variability for a subject.

For instance, a computing device can include a (e.g., piezoelectric) sensor wearable on a subject's wrist that can generate a signal representing vibrations originating from a blood vessel of the subject. In this context, the vibrations are indicative of heart beats and/or respirations of the subject. The computing device can use the signal to determine first times elapsed between respective pairs of consecutive heart beats indicated by the vibrations and/or second times elapsed between respective pairs of consecutive respirations indicated by the vibrations. The computing device can then use the determined first times elapsed to determine a heart rate variability of the subject and/or the determined second times elapsed to determine a respiration rate variability of the subject.

Figure 1:
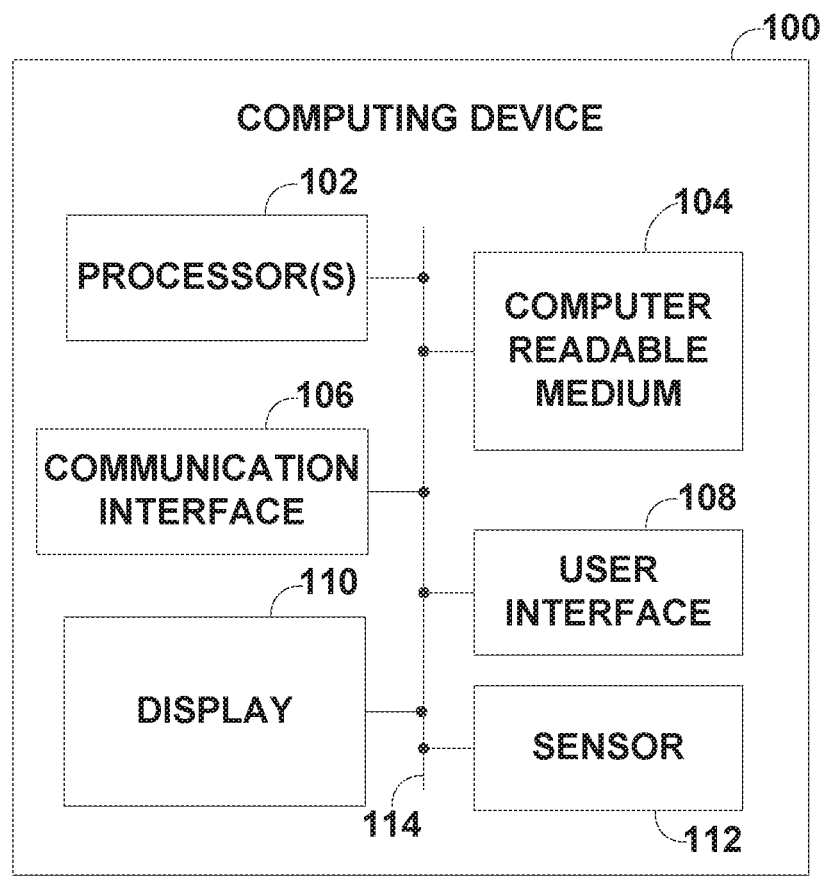
FIG. 1 is a schematic diagram of a computing device, according to an example embodiment.

FIG. 1 is a simplified block diagram of an example computing device 100 that can perform various acts and/or functions, such as any of those described in this disclosure. The computing device 100 can be a mobile phone, a tablet computer, a laptop computer, a desktop computer, a wearable computing device (e.g., in the form of a wrist band), among other possibilities.

The computing device 100 includes one or more processors 102, a computer readable medium 104, a communication interface 106, a user interface 108, a display 110, and a sensor 112. These components as well as other possible components can connect to each other (or to another device or system) via a connection mechanism 114, which represents a mechanism that facilitates communication between two or more devices or systems. As such, the connection mechanism 114 can be a simple mechanism, such as a cable or system bus, or a relatively complex mechanism, such as a packet-based communication network (e.g., the Internet). In some instances, a connection mechanism can include a non-tangible medium (e.g., where the connection is wireless).

The one or more processors 102 can include a general-purpose processor (e.g., a microprocessor) and/or a special-purpose processor (e.g., a digital signal processor (DSP)). In some instances, the computing device 100 may include more than one processor to perform functionality described herein.

The computer readable medium 104 can include one or more volatile, non-volatile, removable, and/or non-removable storage components, such as magnetic, optical, or flash storage, and/or can be integrated in whole or in part with the one or more processors 102. As such, the computer readable medium 104 may take the form of a non-transitory computer-readable storage medium, having stored thereon program instructions (e.g., compiled or non-compiled program logic and/or machine code) that, when executed by the one or more processors 102, cause the computing device 100 to perform one or more acts and/or functions, such as those described in this disclosure. Such program instructions can define and/or be part of a discrete software application. In some instances, the computing device 100 can execute program instructions in response to receiving an input, such as from the communication interface 106 and/or the user interface 108. The computer readable medium 104 can also store other types of data, such as those types described in this disclosure.

The communication interface 106 can allow the computing device 100 to connect to and/or communicate with another device or system according to one or more communication protocols. The communication interface 106 can be a wired interface, such as an Ethernet interface or a high-definition serial-digital-interface (HD-SDI). The communication interface 106 can additionally or alternatively include a wireless interface, such as a cellular or WI-FI interface. A connection provided by the communication interface 106 can be a direct connection or an indirect connection, the latter being a connection that passes through and/or traverses one or more entities, such as such as a router, switcher, or other network device. Likewise, a transmission to or from the communication interface 106 can be a direct transmission or an indirect transmission.

The user interface 108 can facilitate interaction between the computing device 100 and a user of the computing device 100, if applicable. As such, the user interface 108 can include input components such as a keyboard, a keypad, a mouse, a touch sensitive and/or presence sensitive pad or display, a microphone, a camera, and/or output components such as a display device (which, for example, can be combined with a touch sensitive and/or presence sensitive panel), a speaker, and/or a haptic feedback system. More generally, the user interface 108 can include any hardware and/or software components that facilitate interaction between the computing device 100 and the user of the computing device 100.

In a further aspect, the computing device 100 includes the display 110. The display 110 may be any type of graphic display. As such, the display 110 may vary in size, shape, and/or resolution. Further, the display 110 may be a color display or a monochrome display.

The sensor 112 can take the form of a piezoelectric sensor, a pressure sensor, a capacitive sensor, a strain sensor, a force sensor, an optical wavelength selective reflectance or absorbance measurement system, a tonometer, an ultrasound probe, a plethysmograph, or a pressure transducer. Other examples are possible. The sensor 112 is configured to detect vibrations originating from a blood vessel of a subject as further described herein.

Throughout this document, the phrase "a sensor of a computing device" can refer to embodiments where the sensor is integrated with and/or has a wired connection with the computing device. Additionally, "a sensor of a computing device" can refer to embodiments where the sensor has a permanent, impermanent, and/or intermittent wireless connection to the computing device. In some embodiments, the term "computing device" can collectively refer to a "master" device such as a tablet computer, a laptop computer, a desktop computer, or a mobile phone and a "slave device" such as a sensor that has a wireless connection to the master device.

FIG. 2 depicts one embodiment of the computing device 100 and the sensor 112. In FIG. 2, the sensor 112 takes the form of a wearable wristband that is worn by a human subject and the computing device 100 takes the form of a mobile phone. The sensor 112 can detect vibrations originating from a blood vessel (e.g., artery or vein) at the subject's wrist and wirelessly transmit (e.g., via Bluetooth®) to the computing device 100 a signal representing the detected vibrations. The computing device 100 can receive the signal for further processing as described further herein.

Figure 3A:
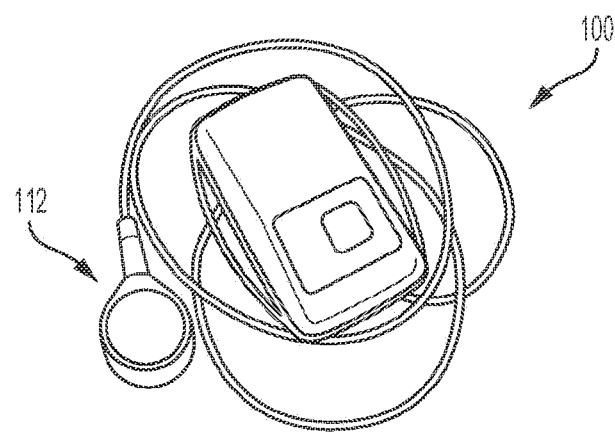
FIG. 3A depicts a computing device, according to an example embodiment.

FIG. 3A depicts another embodiment of the computing device 100. In FIG. 3A, the computing device 100 is communicatively coupled to the sensor 112 via a wired connection.

Figure 3B:
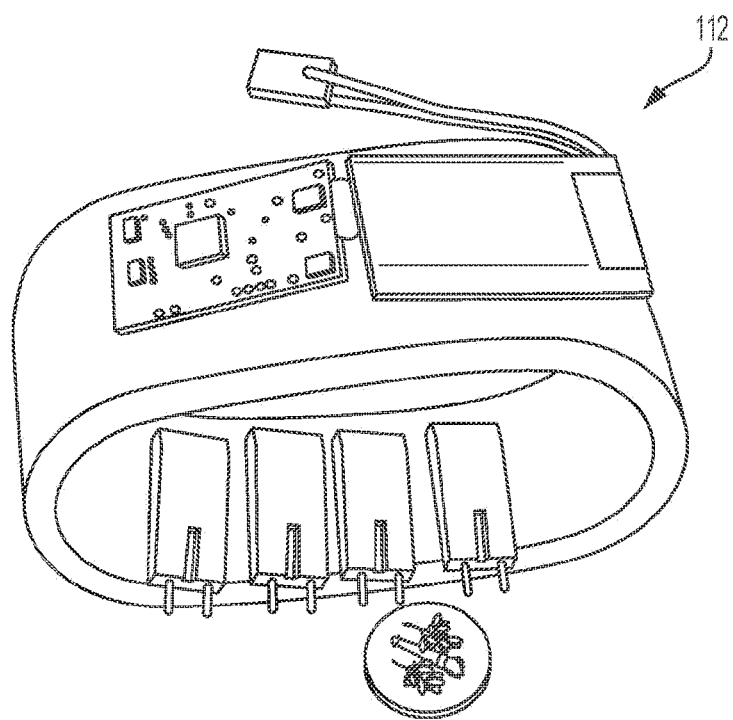
FIG. 3B depicts a sensor, according to an example embodiment.

FIG. 3B depicts an embodiment of the sensor 112, taking the form of a wristband.

Figure 4:
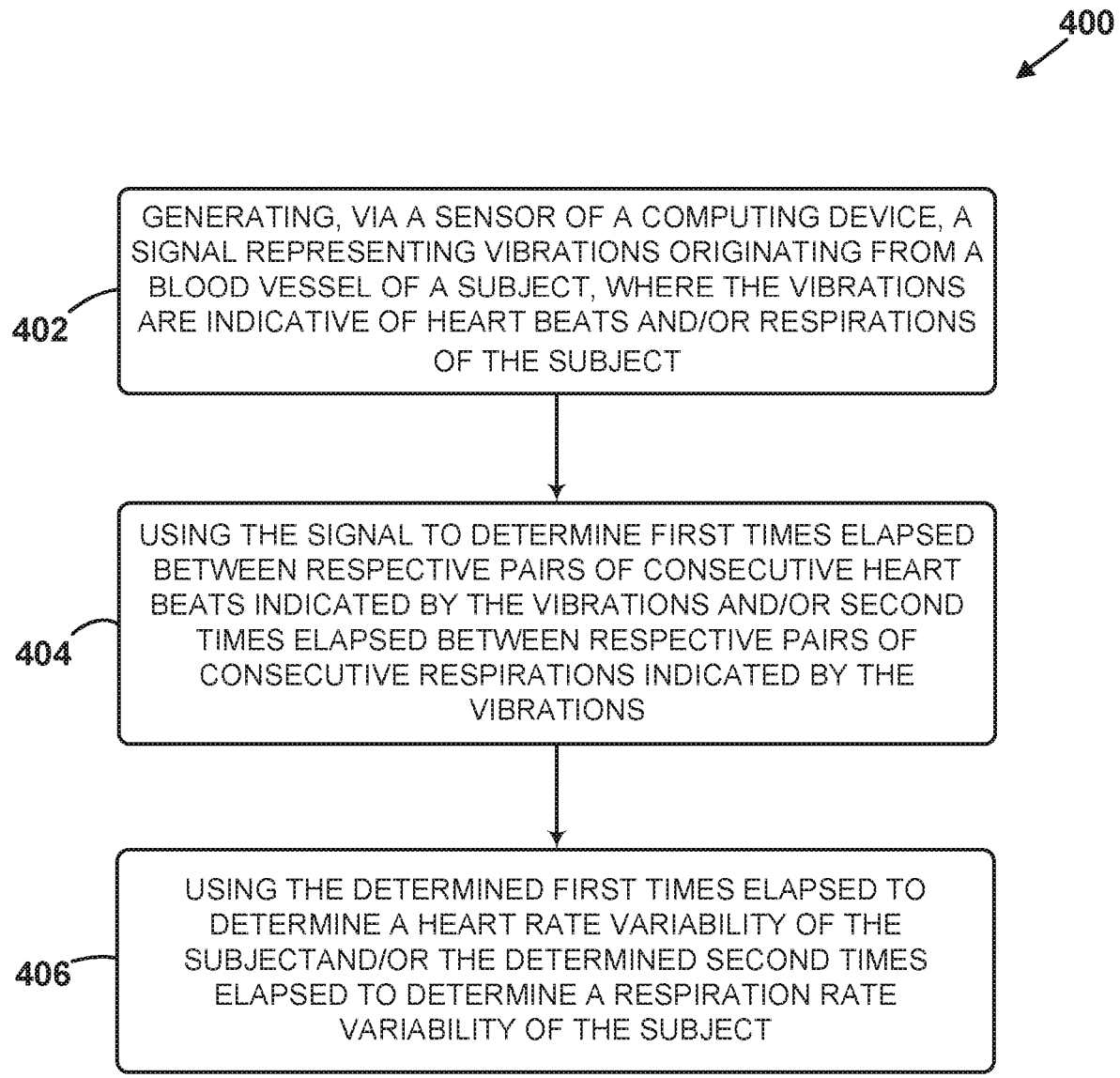
FIG. 4 is a block diagram of a method, according to an example embodiment.

FIG. 4 is a block diagram of a method 400 that can be performed by and/or via the use of the computing device 100.

At block 402, the method 400 includes generating, via a sensor of a computing device, a signal representing vibrations originating from a blood vessel of a subject. In this context, the vibrations are indicative of heart beats and/or respirations of the subject.

For example, the computing device 100, via the sensor(s) 112, can detect vibrations originating from a blood vessel (e.g., a vein wall or an artery wall) of a subject. The sensor(s) 112 can, for example, be positioned proximately to a peripheral vein or a peripheral artery (e.g., at a wrist) of the subject to detect vibrations that originate from the peripheral vein or the peripheral artery. The computing device 100 can then generate a signal representing the detected vibrations.

The vibrations can be produced by fluid flowing through the blood vessel, can be produced by wall tension of the blood vessel, or can be produced by contraction or relaxation of the blood vessel in (e.g., physiological) response to the fluid flowing through the blood vessel or by respirations of the subject.

In a specific example, the sensor(s) 112 can be secured (e.g., via a VELCRO™ strap) to the subject's skin above or near the blood vessel (see FIG. 2). In this case, the blood vessel could be the antebrachial vein. The sensor(s) 112 can detect the vibrations caused by blood flow through the blood vessel as the vibrations are conducted through tissues such as the subject's skin.

The subject can be human, but other animals are possible. As the sensor(s) 112 detects the vibrations, the subject can be breathing spontaneously, e.g., without the aid of a mechanical ventilator, or with the aid of a mechanical ventilator.

Figure 5:
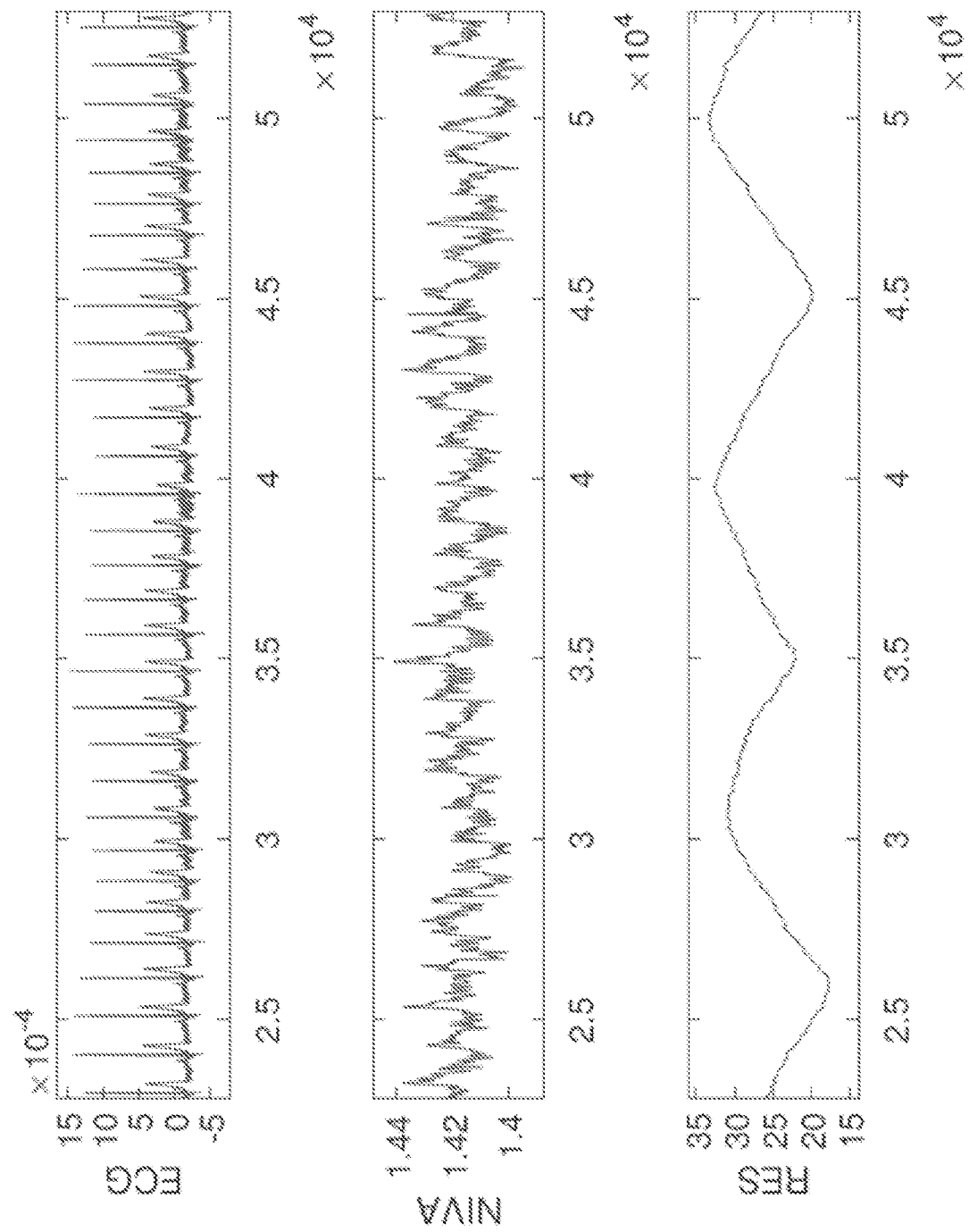
FIG. 5 depicts ECG, NIVA, and respiratory signals for a subject, according to an example embodiment.

Referring to FIG. 5, the signal labeled "NIVA" (non-invasive venous waveform analysis) represents a signal that was generated by a sensor such as the sensor 112 as described above. The NIVA signal can represent a degree of sensor displacement caused by blood vessel vibrations over time. The signal labeled "ECG" was obtained from the same subject using an electrocardiogram at the same time that the NIVA signal was obtained. The ECG signal represents a voltage representing various stages of the subject's heart beat detected at the subject's skin over time. The signal labeled "RES" was obtained from the same subject wearing an expandable chest band at the same time that the NIVA signal was obtained. The RES signal represents expansion and contraction of the subject's chest due to respiration over time. NIVA (e.g., the techniques disclosed herein) has been shown capable of obtaining signals suitable for accurately determining subject respiratory rate, similar to signals obtained using ECG or expandable chest bands, for example.

At block 404, the method includes using the signal to determine first times elapsed between respective pairs of consecutive heart beats indicated by the vibrations and/or second times elapsed between respective pairs of consecutive respirations indicated by the vibrations. For example, the computing device 100 can use the NIVA signal to determine first times elapsed between respective pairs of consecutive heart beats indicated by the vibrations and/or second times elapsed between respective pairs of consecutive respirations indicated by the vibrations, as described below.

Figure 6:
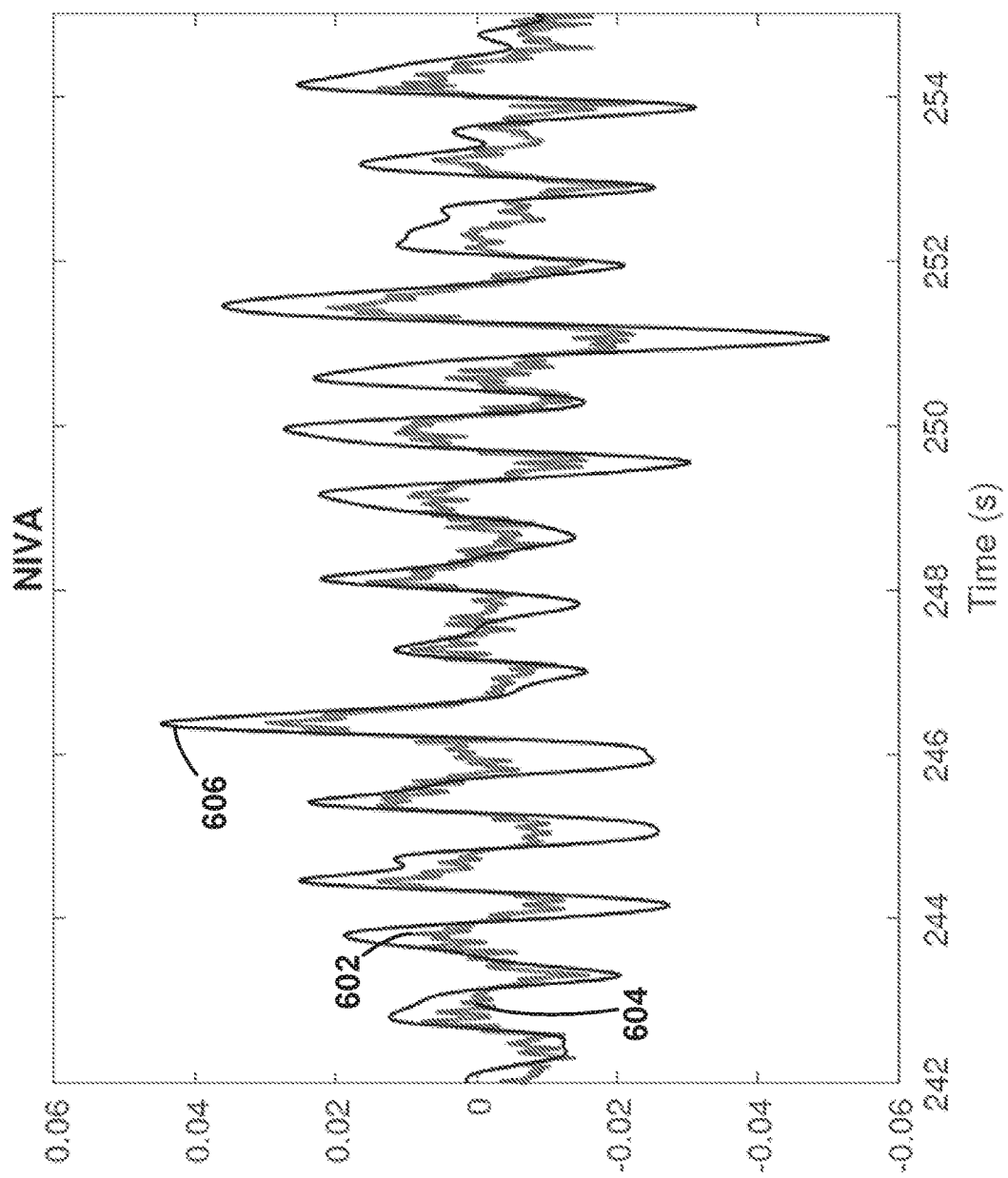
FIG. 6 depicts a raw NIVA signal, a filtered NIVA signal, and an amplified NIVA signal for a subject, according to an example embodiment.

As an initial step, the computing device 100 can low pass filter the NIVA signal. Referring to FIG. 6 for example, a raw NIVA signal 602, a low pass filtered NIVA signal 604, and an amplified NIVA signal 606 are shown. The raw NIVA signal 602 represents a signal as generated by the computing device 100. The low pass filtered NIVA signal 604 represents the output of the computing device 100 low pass filtering the raw NIVA signal 602. The amplified NIVA signal 606 represents the output of the computing device 100 amplifying the low pass filtered NIVA signal 604. The depicted amplitudes of the signal 602, the signal 604, and the signal 606 are not necessarily shown to scale.

Figure 7:
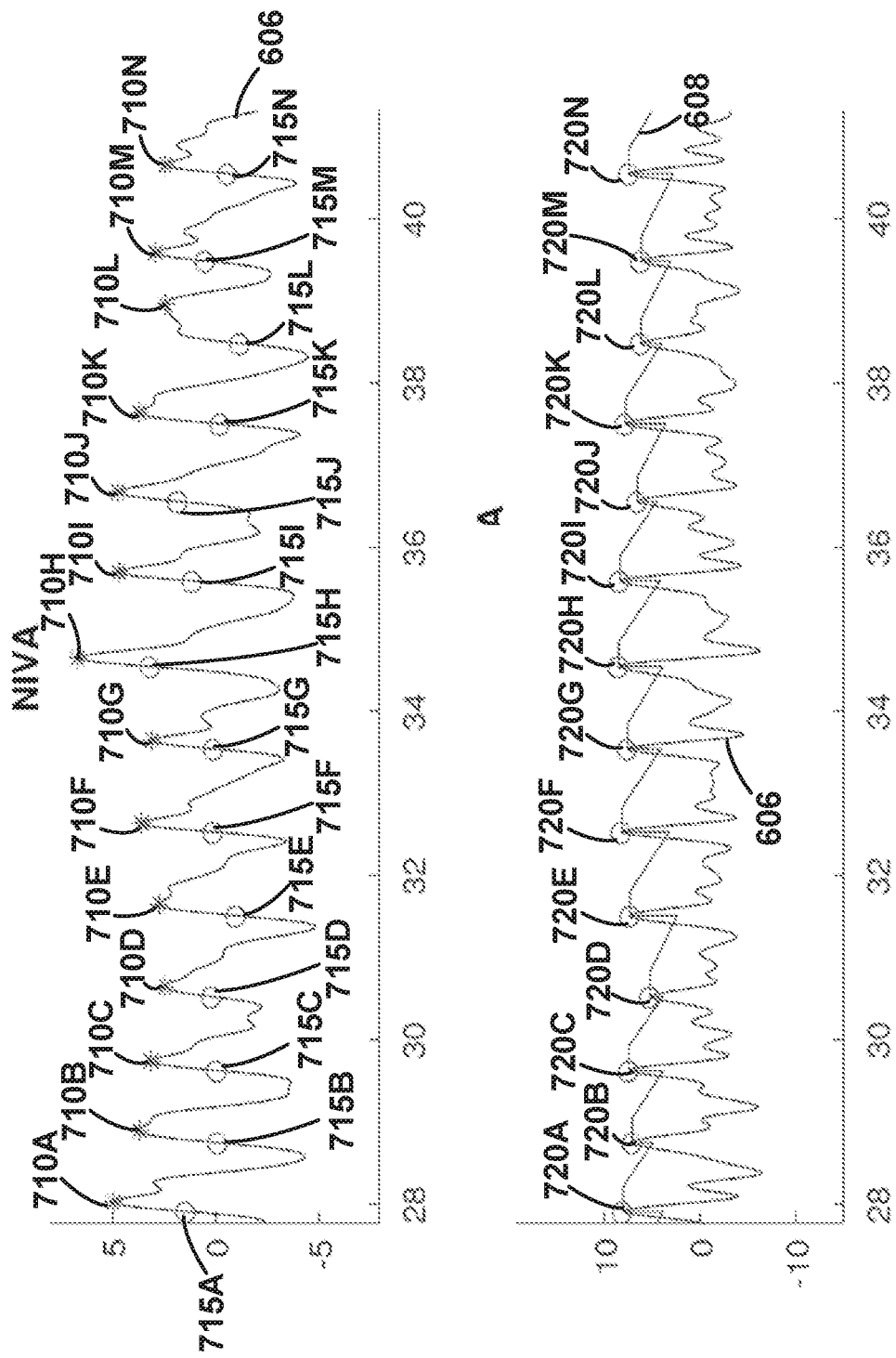
FIG. 7 depicts a NIVA signal and a filtered NIVA signal for a subject, according to an example embodiment.

Referring to FIG. 7, the computing device 100 can then subject the amplified NIVA signal 606 to a low-pass differentiator filter to generate the signal 608. Either the signal 606 or the signal 608 can be used by the computing device 100 for peak identification or maximum slope identification, as described below. The computing device 100 can identify full cycles of NIVA signals in other ways as well. In general, each peak (e.g., full cycle) of the signal 606 or the signal 608 can be thought of as representing a single heartbeat of the subject. Additionally, lower frequency information can be resolved from the signal to obtain respiratory rate and respiratory rate variability.

In some embodiments, the computing device 100 can identify peaks (e.g., local maxima) 710A, 710B, 710C, 710D, 710E, 710F, 710G, 710H, 710I, 710J, 710K, 710L, 710M, and 710N of the signal 606. (In other embodiments, the computing device 100 could also identify local minima of the signal 606). The computing device 100 can identify the peaks using an adaptive threshold, for example. The computing device 100 can then determine the respective times elapsed between the consecutive peaks 710A and 710B, between the consecutive peaks 710B and 710C, between the consecutive peaks 710C and 710D, and so on until determining the time elapsed between the consecutive peaks 710M and 710N. These times elapsed between consecutive heart beats can be further used by the computing device 100, as described below with respect to block 406. Similar techniques can be used to obtain respiratory rate and respiratory rate variability.

In a similar fashion, the computing device 100 could also identify points of maximum (e.g., positive) slope of the signal 606, e.g., points 715A, 715B, 715C, 715D, 715E, 715F, 715G, 715H, 715I, 715J, 715K, 715L, 715M and 715N. (In other embodiments, the computing device 100 could also identify points of maximum negative slope of the signal 606). The computing device 100 can then determine the respective times elapsed between the consecutive points 715A and 715B, between the consecutive points 715B and 715C, between the consecutive points 715C and 715D, and so on until determining the time elapsed between the consecutive points 715M and 715N. These times elapsed between consecutive heart beats can be further used by the computing device 100, as described below with respect to block 406. Similar techniques can be used to obtain respiratory rate and respiratory rate variability.

In some embodiments, the computing device 100 can identify peaks (e.g., local maxima) 720A, 720B, 720C, 720D, 720E, 720F, 720G, 720H, 720I, 720J, 720K, 720L, 720M, and 720N of the signal 608. (In other embodiments, the computing device 100 could also identify local minima of the signal 608). The computing device 100 can identify the peaks using an adaptive threshold, for example. The computing device 100 can then determine the respective times elapsed between the consecutive peaks 720A and 720B, between the consecutive peaks 720B and 720C, between the consecutive peaks 720C and 720D, and so on until determining the time elapsed between the consecutive peaks 720M and 720N. These times elapsed between consecutive heart beats can be further used by the computing device 100, as described below with respect to block 406. Similar techniques can be used to obtain respiratory rate and respiratory rate variability.

At block 406, the method includes using the determined first times elapsed between respective pairs of consecutive heart beats to determine a heart rate variability of the subject and/or the determined second times elapsed to determine a respiration rate variability of the subject. For example, the computing device 100 can use the times elapsed between (i) pairs of consecutive peaks of the peaks 710A-N, (ii) pairs of consecutive points of the points of maximum slope 715A-715N, and/or (iii) pairs of consecutive peaks of the peaks 720A-N to determine the heart rate variability of the subject. Typically, the computing device 100 uses NIVA signals such as the signal 606 or the signal 608 (or unprocessed NIVA signals or NIVA signals processed in other ways) to calculate a variance or a standard deviation etc. of all the times elapsed between consecutive heart beats, e.g., between peaks of a NIVA signal, between local minima or maxima of a NIVA signal, and/or between consecutive points of a NIVA signal having a local absolute maximum in slope. Similar techniques can be used to obtain respiratory rate and respiratory rate variability.

Figure 8:
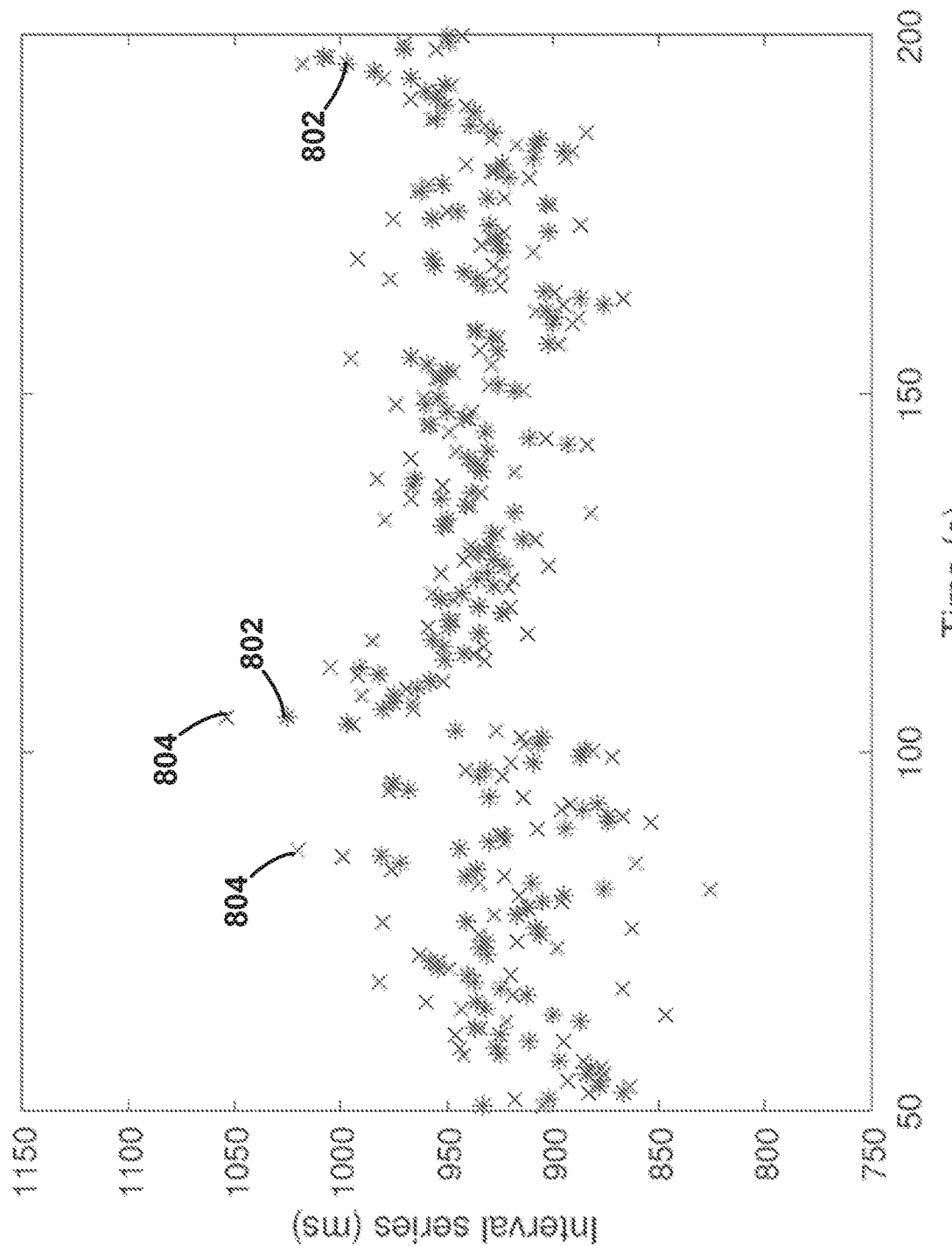
FIG. 8 depicts data indicative of times elapsed between subject heart beats as a function of time, according to an example embodiment.

FIG. 8 is a scatter plot depicting times elapsed between consecutive heart beats as a function of time. The star shaped points represent times elapsed 802 as determined by (e.g., the computing device 100) analyzing an ECG signal (e.g., the ECG signal of FIG. 5). The x-shaped points represent times elapsed 804 as determined by (e.g., the computing device 100) analyzing a NIVA signal (e.g., the NIVA signals 602, 604, 606, or 608). FIG. 8 shows that the times elapsed between this particular subject's consecutive heart beats ranged from about 830 ms to 1050 ms over a duration of about 150 seconds. The time between the subject's heart beats increased slightly over that period of time. Similar data collection techniques can be used to obtain respiratory rate variability.

As such, block 406 can include the computing device 100 calculating a variance of all of the times elapsed 804, perhaps using equation (1) below. In the context of equation (1), $s^2$ is equal to the variance of the times elapsed between the consecutive heart beats of the subject, i refers to each term in the times elapsed data set, $t_M$ refers to the arithmetic mean of all of the times elapsed between the consecutive heart beats of the subject, and n refers to the quantity of times elapsed in the data set. The calculated variance represents a proxy for the subject's heart rate variability (HRV). In other embodiments, a standard deviation of all of the times elapsed between the consecutive heart beats of the subject can be calculated and used as a proxy for the subject's HRV instead. Other quantitative metrics can also be used as a proxy for HRV.

$$S^2 = \frac{\sum_{1}^{n}(t_i - t_M)^2}{n-1} \quad (1)$$

In various embodiments, it can be useful to use data sets that represent heart beats that all occur within a particular duration of time, e.g., ranging from 1 second to 10 seconds, 2 seconds to 8 seconds, or 2.5 seconds to 6 seconds. These ranges of time will typically correspond to the period of the subject's respiration. NIVA techniques themselves can be used to determine the subject's actual respiratory rate and a time window can be selected based on the determined respiratory rate. By focusing on a period of time that corresponds somewhat closely to the subject's actual respiratory rate, data that is more representative of the subject's parasympathetic response can be obtained. Heightened parasympathetic response generally corresponds with a higher HRV in the frequency range of approximately 0.15 to 0.4 Hz.

Figure 9:
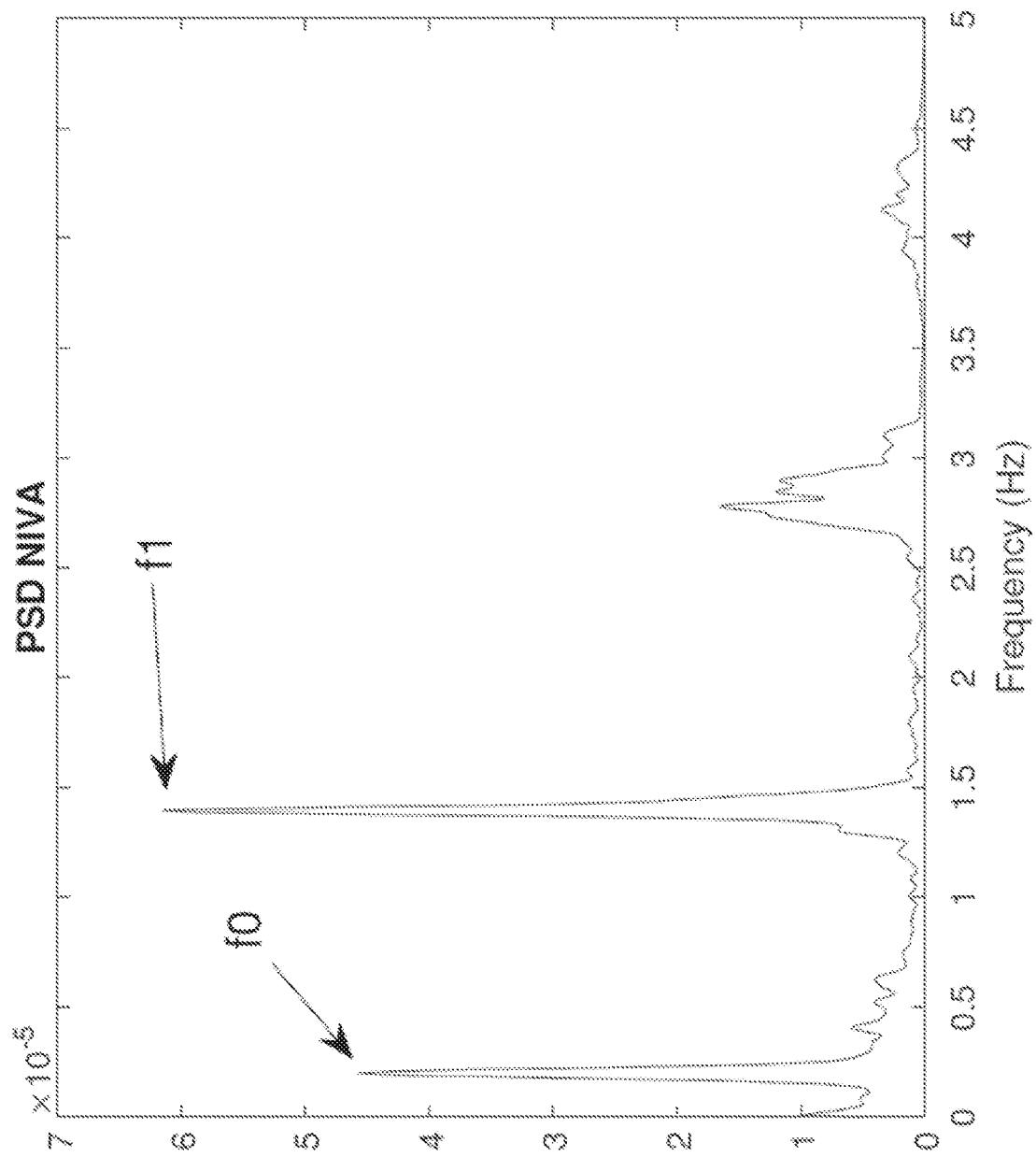
FIG. 9 depicts a power spectral density of a NIVA signal for a subject, according to an example embodiment.

FIG. 9 shows a power spectral density of a NIVA signal. For example, the computing device 100 can obtain a power spectral density of a NIVA signal such as the signals 602, 604, 606, or 608 by performing a Fourier transform upon the NIVA signal. Next, the computing device 100 can determine a lowest frequency of the power spectral density at which a peak exceeding a predetermined power threshold exists. In FIG. 9, for example, the predetermined threshold power might be set at $1 \times 10^{-5}$ arbitrary units, with f0 being the lowest frequency of the power spectral density at which a peak exceeding the threshold exists. As such, the peak "f0" corresponds to the subject's respiratory rate, which in this case is about 0.2 Hz. The peak "f1" corresponds to the subject's heart rate, which in this case is about 1.45 Hz.

In this example, the subject's respiratory rate of 0.2 Hz corresponds to a reciprocal time window of 5 seconds. As such, the computing device 100 might generate a NIVA signal for at least 5 seconds, or perhaps for 10 seconds, and calculate a variance or standard deviation of the times elapsed between consecutive heart beats within that time window. In another embodiment, the computing device 100 can generate several minutes worth of NIVA data to calculate several variances, with each variance corresponding to a distinct window of time that lasts about 5 to 10 seconds (or another duration of time). The time windows that correspond to the subject's respiratory rate (e.g., several seconds) should have information most representative of parasympathetic response, but performing the measurement several times over the course of several minutes can help achieve better accuracy. Such data can be used to evaluate a subject's parasympathetic nervous system response based on the determined heart rate variability. Variances of data corresponding to times elapsed between consecutive heart beats over larger windows of time (e.g., minutes) can be used to evaluate a subject's sympathetic nervous system response based on the determined heart rate variability.

The methods disclosed herein can be used to evaluate the efficacy of treatment protocols such as pain medication, anti-depressants, yoga, oxytocin administration, narcotics administration, sedative administration, anxiolytics administration, behavioral therapeutic interventions, sympathetic colitics administration, alpha and beta antagonists administration, environmental interventions (e.g., subject exposure to decreased light compared to control or decreased noise compared to control), music therapy, art therapy, virtual reality therapy, pet therapy, or the like.

The disclosed methods can be used to treat or diagnose post-traumatic stress disorder, anxiety, pain, depression, delirium, critical illness, post-surgical stress, traumatic brain injury, cancer, post-myocardial infarction, complications caused by local anesthesia or conscious sedation, burns, or complications of childbirth.

For example, the disclosed methods can be used to evaluate the efficacy of treatments for PTSD such as psychotherapy or antidepressants. Such antidepressants might also be used to help symptoms of depression and anxiety. They can also help improve sleep problems and concentration. Such medications might include the selective serotonin reuptake inhibitor (SSRI) medications sertraline (Zoloft) and paroxetine (Paxil), or Prazosin.

The disclosed methods can also be used to evaluate the efficacy of treatments for anxiety such as psychotherapy and antidepressants, including medications in the selective serotonin reuptake inhibitor (SSRI) and serotonin and norepinephrine reuptake inhibitor (SNRI) classes. Examples of antidepressants used to treat generalized anxiety disorder include escitalopram (Lexapro), duloxetine (Cymbalta), venlafaxine (Effexor XR) and paroxetine (Paxil, Pexeva), Buspirone, or Benzodiazepines.

The disclosed methods can also be used to evaluate the efficacy of treatments for depression such as SSRIs including citalopram (Celexa), escitalopram (Lexapro), fluoxetine (Prozac), paroxetine (Paxil, Pexeva), sertraline (Zoloft), and vilazodone (Viibryd), or Serotonin-norepinephrine reuptake inhibitors (SNRIs). Examples of SNRIs include duloxetine (Cymbalta), venlafaxine (Effexor XR), desvenlafaxine (Pristiq, Khedezla) and levomilnacipran (Fetzima). The disclosed methods can also be used to evaluate efficacy of bupropion (Wellbutrin XL, Wellbutrin SR, Aplenzin, Forfivo XL), mirtazapine (Remeron), nefazodone, trazodone and vortioxetine (Trintellix). The disclosed methods can also be used to evaluate efficacy of tricyclic antidepressants such as imipramine (Tofranil), nortriptyline (Pamelor), amitriptyline, doxepin, trimipramine (Surmontil), desipramine (Norpramin) and protriptyline (Vivactil). The disclosed methods can also be used to evaluate efficacy of monoamine oxidase inhibitors (MAOIs) such as tranylcypromine (Parnate), phenelzine (Nardil) and isocarboxazid (Marplan) Selegiline (Emsam).

Figure 10:
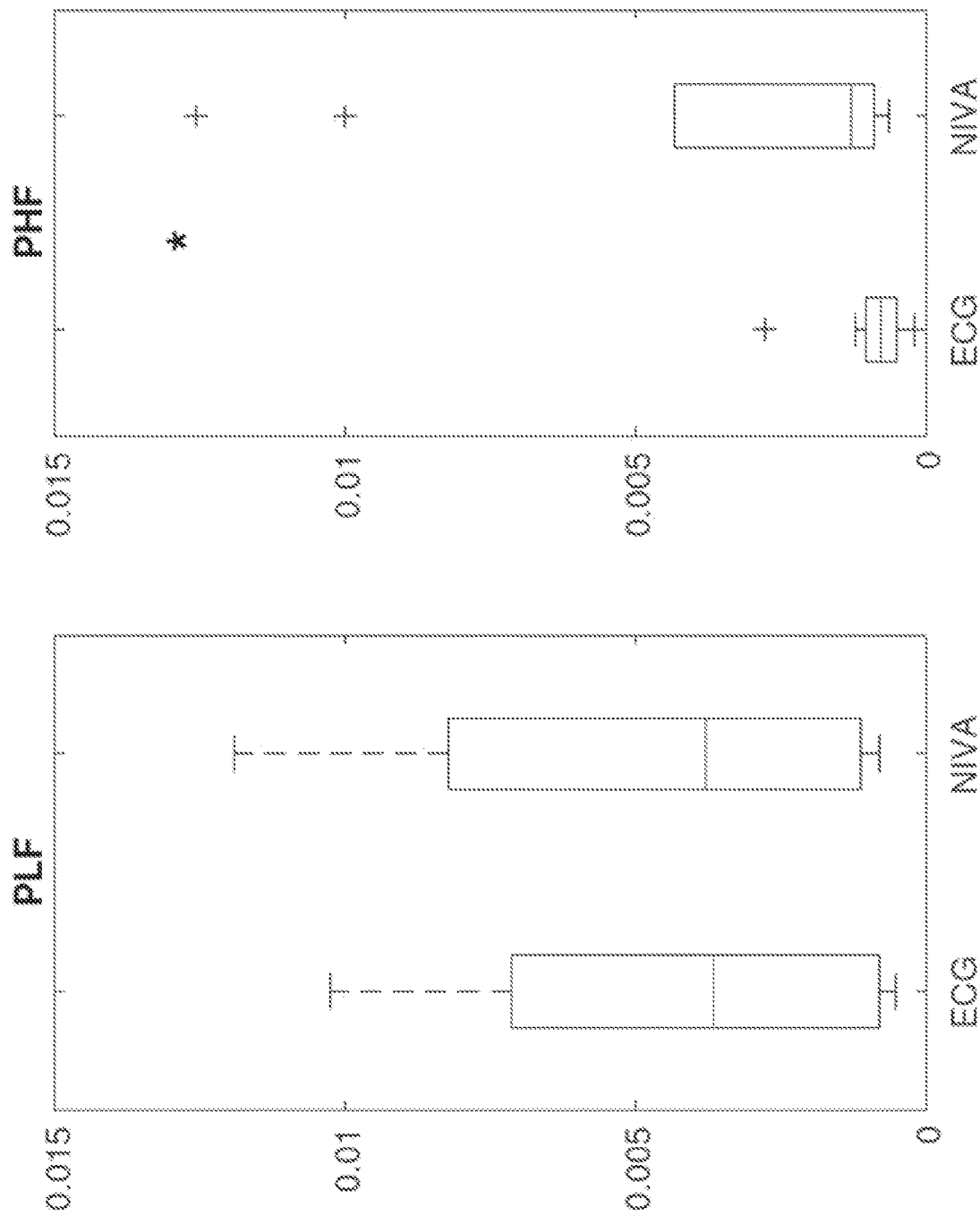
FIG. 10 depicts relative signal power at low frequency and at high frequency for ECG and NIVA, according to an example embodiment.

FIG. 10 shows the general relationship between the signal power for ECG and NIVA obtained from a subject at the same time. As shown, at low frequencies (PLF) (e.g., 0.04 to 0.15 Hz) the NIVA and ECG signals have similar signal-to-noise ratio (SNR), while at high frequencies (PHF) (e.g., 0.15 to 0.4 Hz) NIVA has a noticeably higher SNR.

Figure 11:
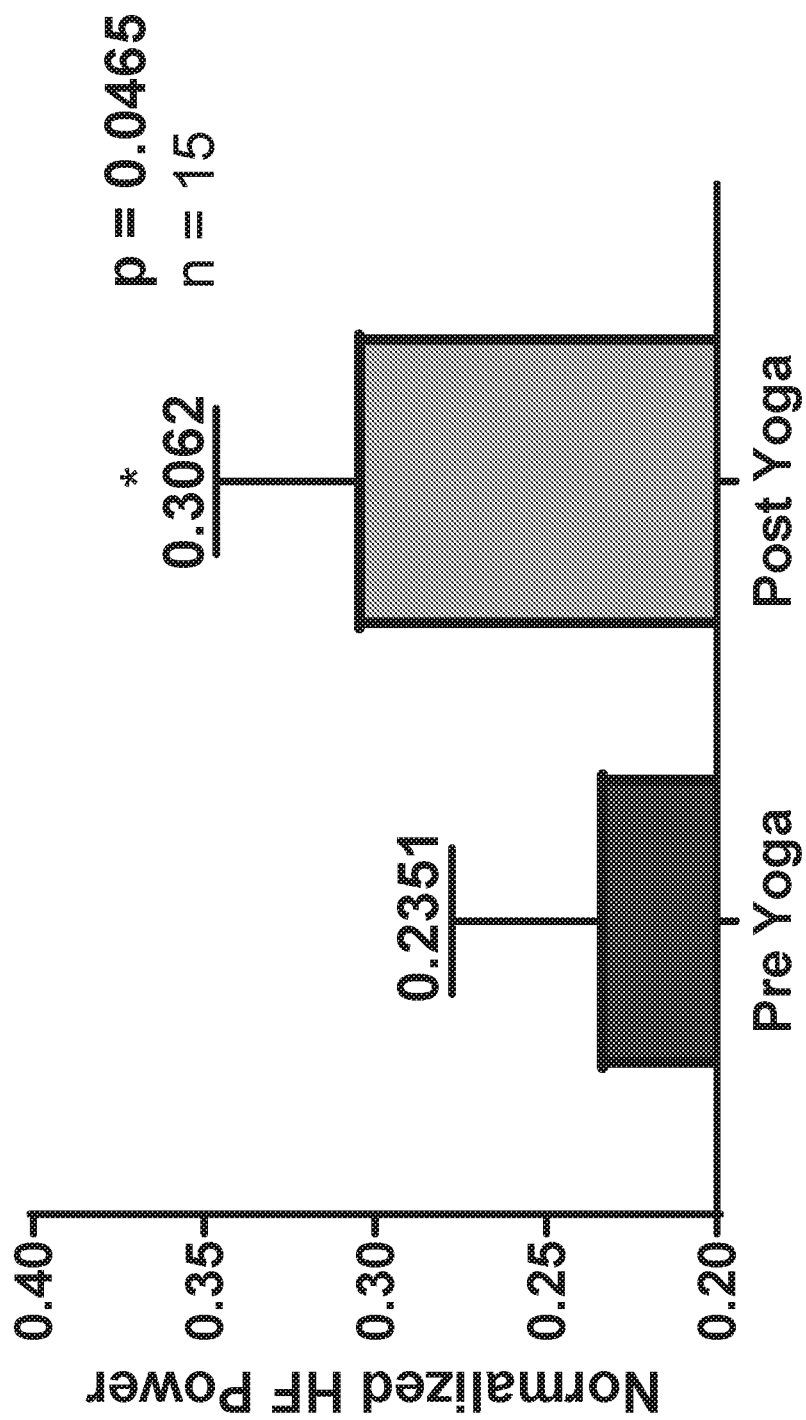
FIG. 11 depicts normalized signal power corresponding to HRV calculated over a period of time that corresponds to a respiratory rate of a subject, evaluated prior to and after performance of yoga exercises, according to an example embodiment.

FIG. 11 depicts data corresponding to 15 subjects, collected before and after the subjects performed yoga exercises. The data shows higher HRV within the frequency ranges that correspond to subject respiration rate (e.g., 0.04 to 0.15 Hz) after the subjects perform yoga exercises. More specifically, in this experiment, the frequency range was defined as each subject's detected respiratory rate +/−0.025 Hz. This data indicates that the yoga exercises can lead to the activation of the subjects' parasympathetic nervous system.

The following text includes discussion of further experimental results.

Figure 12:
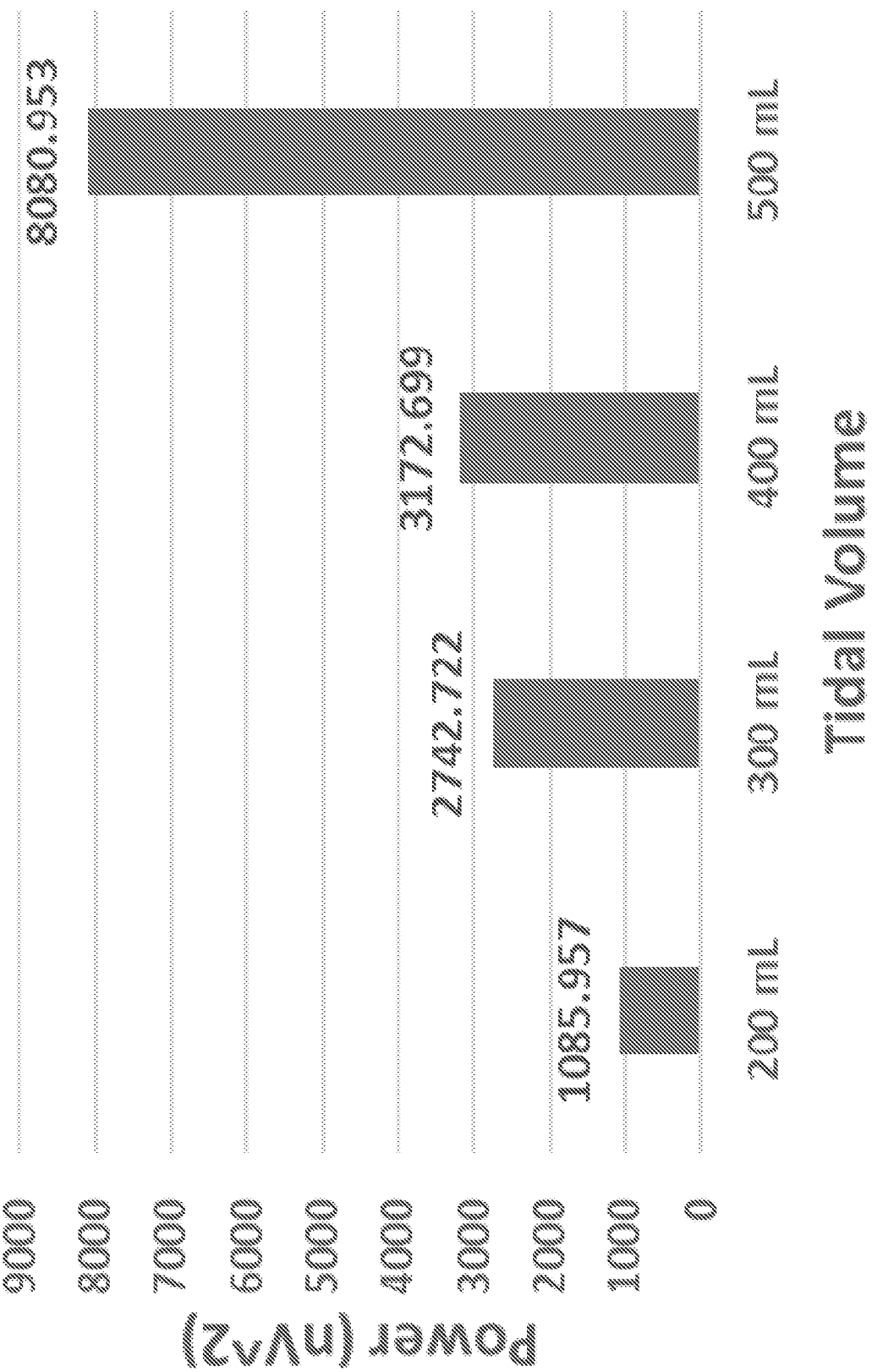
FIG. 12 depicts a relationship between respiratory rate peak power and tidal volume in a porcine model.

FIG. 12 depicts a relationship between respiratory rate peak power and tidal volume in a porcine model. As shown, peak signal power generally correlates with tidal volume.

Figure 13:
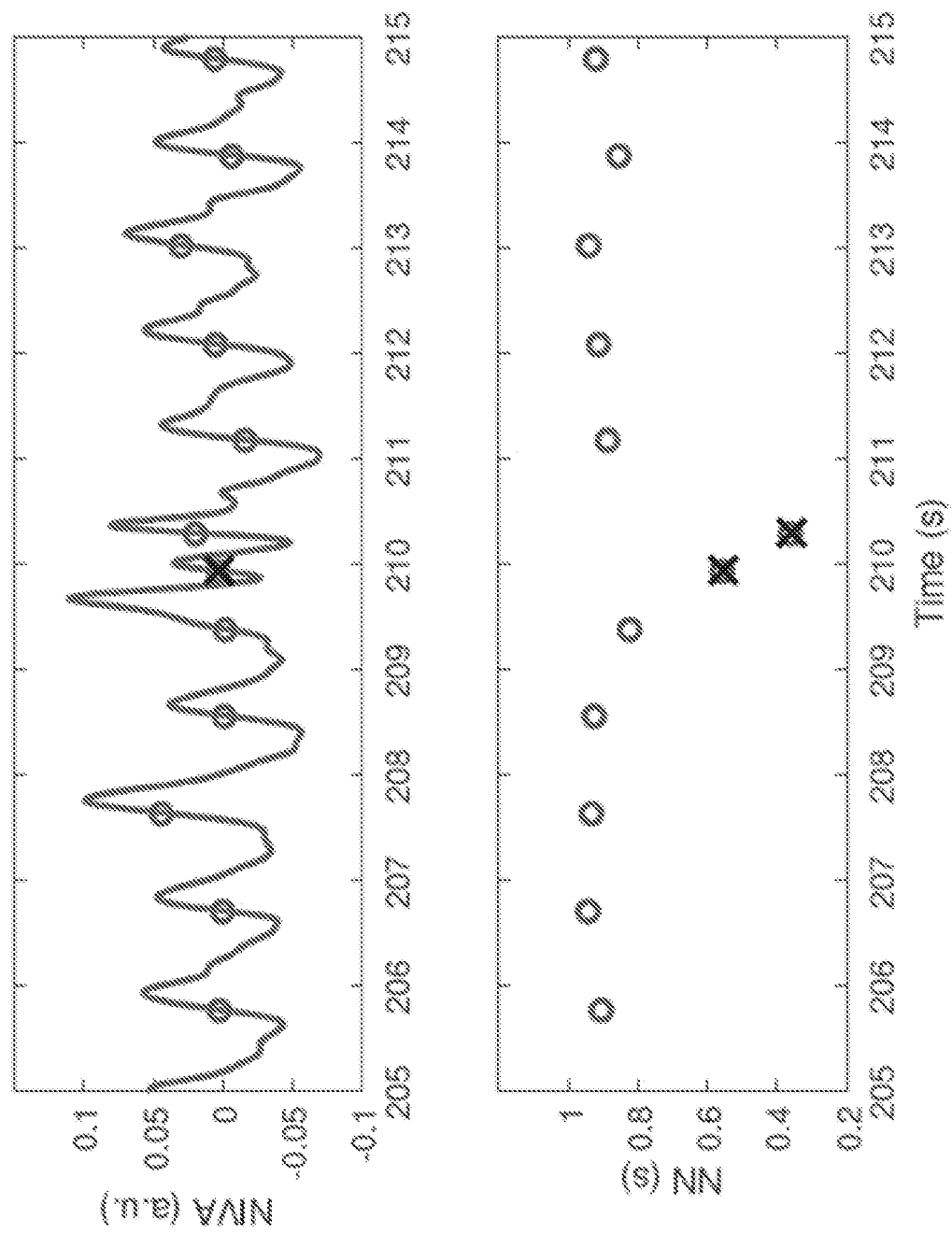
FIG. 13 depicts a NIVA waveform (upper panel) with pulse detections (circles) including an incidence (cross), and a corresponding pulse interval series (lower panel) with outlier intervals removed.

FIG. 13 depicts a NIVA waveform (upper panel) with pulse detections (circles) including an incidence (cross), and a corresponding pulse interval series (lower panel) with outlier intervals removed.

Figure 14:
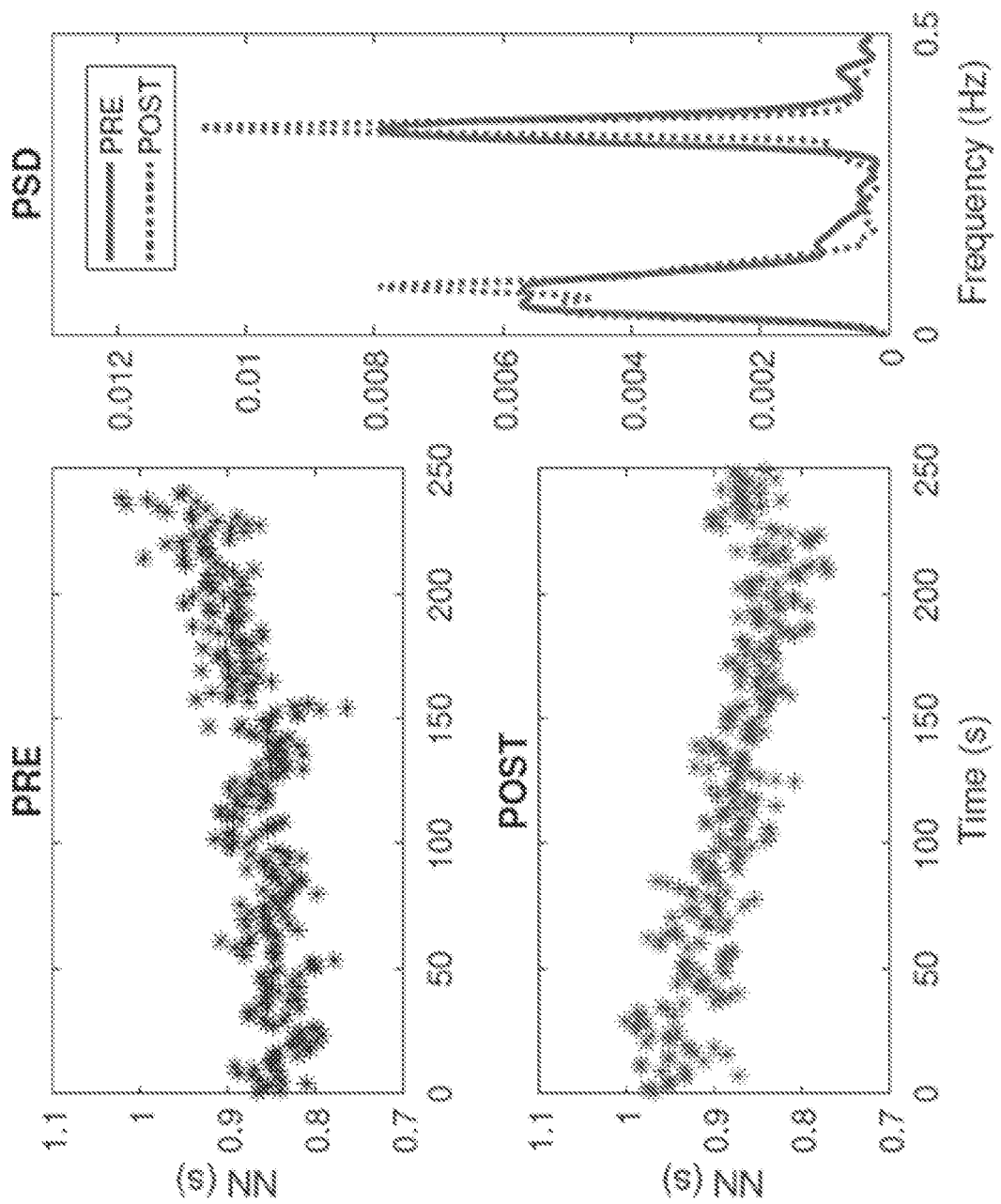
FIG. 14 depicts an NN interval series for pre-yoga and post-yoga sessions (left panels) and their corresponding power spectral densities (right panel).

FIG. 14 depicts an NN interval series for pre-yoga and post-yoga sessions (left panels) and their corresponding power spectral densities (right panels).

Figure 15:
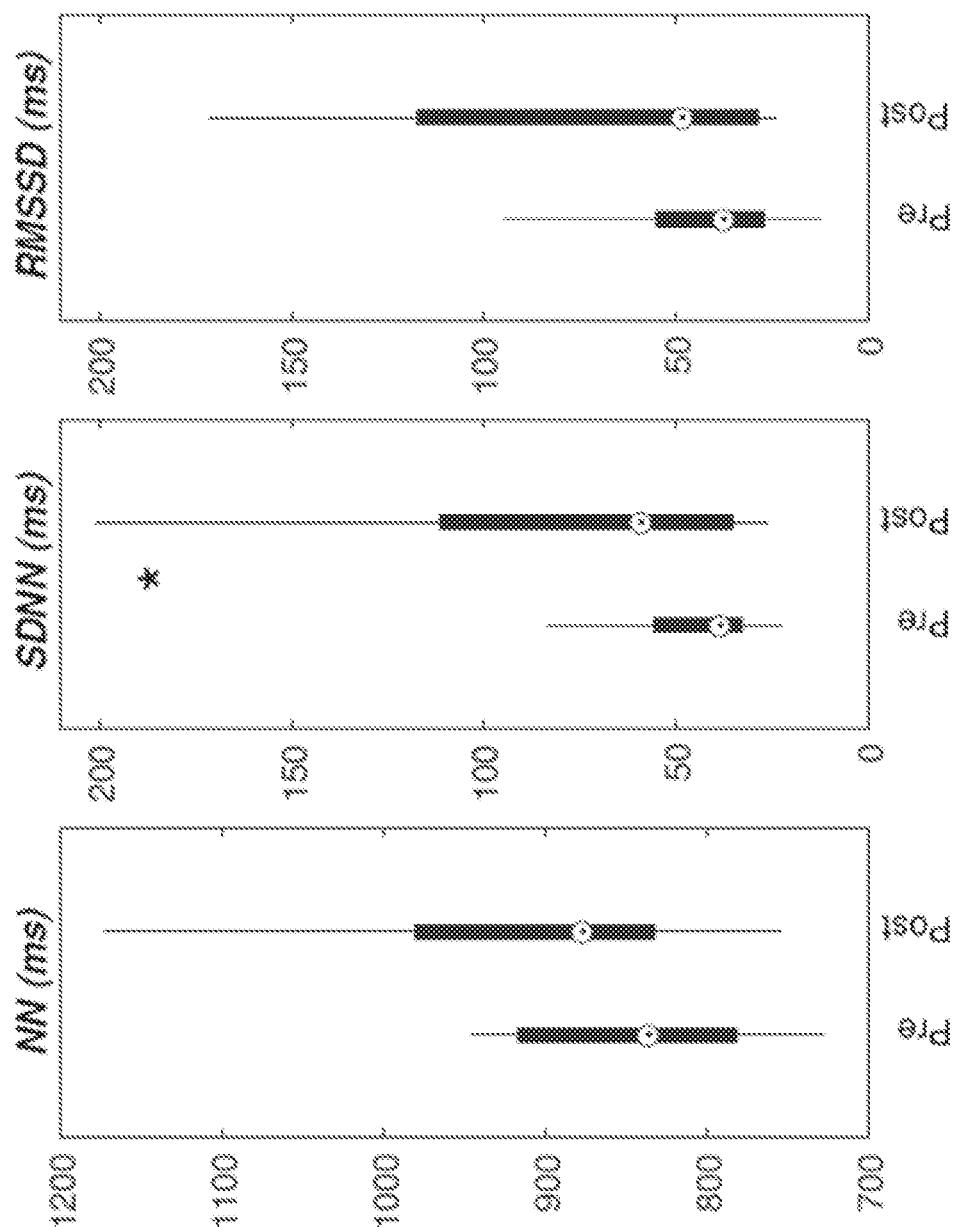
FIG. 15 depicts temporal PRV parameters in pre-yoga and post-yoga recordings.

FIG. 15 depicts temporal PRV parameters in pre-yoga and post-yoga recordings (* denotes significant differences (p<0.05)).

Figure 16:
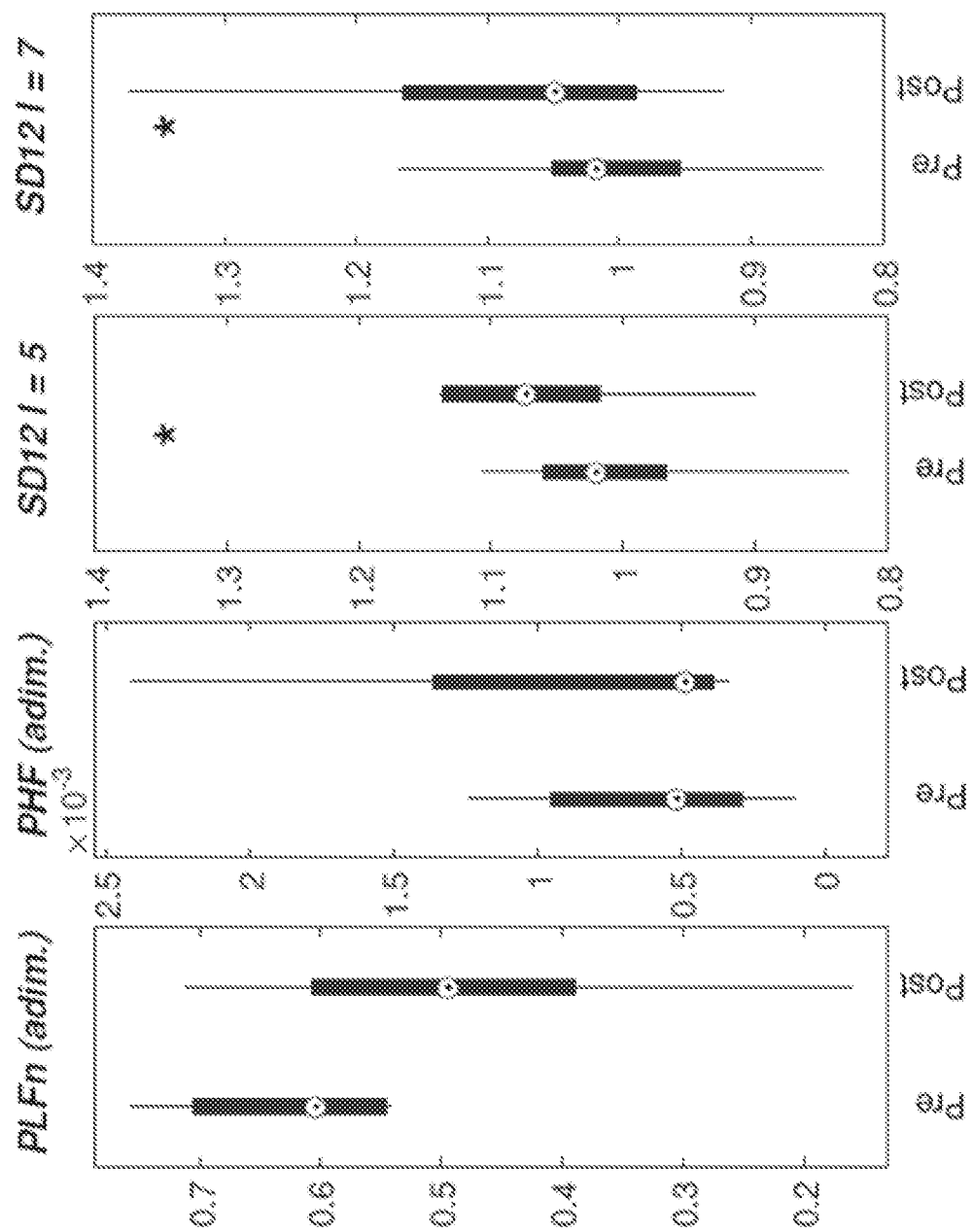
FIG. 16 depicts spectral and LLP (SD12, lags 5 and 7) PRV parameters in pre-yoga and post-yoga recordings.

FIG. 16 depicts spectral and LLP (SD12, lags 5 and 7) PRV parameters in pre-yoga and post-yoga recordings (* denotes significant differences (p<0.05)).

The benefits of yoga have been studied in different fields, from chronic health conditions to mental disorders, showing that it can help to improve overall health. In particular, it has been shown that yoga can improve autonomic function. Heart rate variability (HRV) at rest is commonly used as a non-invasive measure of autonomic regulation of heart rate. Alternatively, pulse rate variability (PRV) has been proposed as a surrogate of HRV. This study aims to assess the effect of yoga in the autonomic nervous system by analyzing the PRV obtained from the NIVA signal. Temporal (statistics of the normal-to-normal intervals), spectral (power in low and high frequency bands) and nonlinear (lagged Poincare'Plot analysis) parameters are analyzed before and after a yoga session in 20 healthy volunteers. The PRV analysis shows an increase in parameters related to parasympathetic activity and overall variability, and a decrease in parameters related to sympathetic activity and mean heart rate. These results support the beneficial effect of yoga in autonomic nervous system, increasing the parasympathetic activity.

Several studies have taken advantage of the peripheral venous line in hospitalized patients, used primarily to allow fluids and medications to be given directly into the circulatory system, to derive patients' hemodynamic information. For example, continuous monitoring of intravascular volume status was used to detect early Stage 1 hemorrhage, while other physiological parameters such as heart rate, $SpO_2$ or mean arterial pressure did not show any differences. Also, peripheral venous signal is able to not only give the volume status of the patient, but also additional information such as the respiratory rate and pulse rate.

This capability to offer valuable additional information raises the interest of obtaining this signal in a non-invasive way that will allow a continuous monitoring in daily life. Non-Invasive Venous waveform Analysis (NIVA) can obtain information on volume status, heart rate, and respiratory rate. Results have showed that high frequency power was significantly higher in PRV analysis from NIVA than in heart rate variability (HRV) from ECG, suggesting that the NIVA signal may enhance measurement of parasympathetic activity.

Some authors have studied the effect of yoga on the autonomic function via HRV analysis, showing an increase in parasympathetic activity. We obtained both temporal and spectral PRV parameters with a NIVA band before and after a yoga session in 20 volunteers. In addition, we propose the Lagged Poincare'Plot (LPP) for nonlinear analysis of PRV series. Significant differences were already found in Poincare'Plot parameters, when they were used together with time and frequency analyses of heart rate variability, to study autonomic regulation in yogic and control groups of subjects. Moreover, LPP has been shown to be reliable for ultra-short time HRV analysis.

In the study, there were 5 men and 15 women with an age range of (27-79, mean 52, median 56). The subjects reclined in savanna position with the head and lower extremities supported with blankets. Venous waveform signals were collected for 5-6 minutes, before (pre-yoga) and after (post-yoga) a 2 hour "awareness yoga" session, which is a slow restorative type of relaxation yoga. Venous waveforms were collected using a piezoelectric sensor placed on the volar aspect of the wrist overlying the venous plexus, secured with an elastic wrap. The sensor was interfaced with a prototype NIVA device (which contains an amplifier, microcontroller, and flash memory). The data was transferred to a computer as text files using a USB cable and analyzed as described below.

The NIVA signal is first low-pass filtered with a cut-off frequency of 5 Hz to remove high frequency noise. Frequencies below 0.3 Hz are also removed using a high-pass filter to remove low oscillations such as the baseline wander. For pulse detection, first a linear-phase FIR low-pass-differentiator (LPD) filter is applied to accentuate the upslopes of the pulses; and then an adaptative threshold is applied to detect the peaks in the LPD filtered signal, which represents the points with maximum slope in the NIVA signal. These k-th pulse detections are denoted as $n_k$.

From $n_k$, the pulse interval series are obtained as $d(k)=n_k-n_{k-1}$. Pulses in NIVA signals are sometimes masked by noise, yielding erroneous or missed pulse detections, which result in outlier (or anomalous) pulse intervals. These outliers are identified and removed, obtaining the normal-to-normal (NN) intervals. FIG. 13 shows an example of pulse detection with an incidence and its correction (upper panel), which also reflects in the NN interval series (lower panel).

For temporal domain analysis, PRV parameters are derived from the NN intervals. Three parameters were considered: the standard deviation of the pulse intervals (SDNN), the square root of the mean squared differences of successive pulse intervals (RMSSD) and the mean pulse interval time ($\overline{NN}$).

For frequency domain analysis, PRV parameters are derived from the modulating signal m(n), which is assumed to have information about ANS activity, and is computed and described below. The instantaneous pulse rate signal, $d_{PR}(n)$, is derived from d(k), following a method based on the time-varying integral pulse frequency modulation (TVIPFM) model, and resampled at 4 Hz. This signal is high-pass filtered to remove the mean heart rate tendency $d_{PRM}(n)$ (very low frequency components) and corrected to obtain the pulse rate modulating signal $m(n)=(d_{PR}(n)-d_{PRM}(n))/d_{PRM}(n)$.

Although the method takes into account the possible presence of ectopic beats, false or missed detections, if there are too many outliers following each other, the gap is too long and the estimated m(n) can introduce artificial oscillations. Therefore, we generally do not take into account these gaps if they are longer than 3 seconds. In order to have a reliable frequency domain analysis, we only considered segments no shorter than 90 seconds without gaps longer than 3 seconds.

The power spectral density (PSD) of m(n) is computed using the Welch periodogram, with 60 s windows 10 s overlapped. The powers in the LF and HF bands are computed integrating the power spectrum in the corresponding bands: PLF from 0.04 to 0.15 Hz, and PHF from 0.15 to 0.4 Hz. The normalized LF power is obtained as $P_{LFn}=P_{LF}/(P_{LF}+P_{HF})$.

The Poincare'Plot is a graphical representation of inter-beat dynamics, inspired by the return map theory to describe the phase space trajectories. In the standard version, the Poincare'Plot is a scatterplot where each pulse interval d(k) is plotted against the immediately previous pulse interval d(k−1). In the lagged Poincare'Plot (LPP) technique, a lag 1 is introduced and scatterplots are made by the points with coordinates d(k) and d(k−1). Previous studies investigated a range of lag values equals to $1 \leq l \leq 10$.

The most used quantitative approach to describe the shape of LPP is the ellipse fitting technique. Following this methodology, the LPP is turned 45° clockwise and the two standard deviations of the points around the vertical (SD1) and horizontal (SD2) axes are computed. SD1 is a measure of the short-term variability of pulse interval series, whereas SD2 describes long-term dynamics. In this study we investigated the two standard deviations, SD1 and SD2, together with their ratio SD12=SD1/SD2.

We computed the values of SD1, SD2, and SD12 in 50% overlapped windows lasting 35 seconds, both in pre-yoga and post-yoga NN intervals. The standard range $1 \leq l \leq 10$ for the lag value was considered in the LPP analyses. The reliability of LPP parameters calculated using the ellipse fitting technique in 35 second windows was already investigated in previous studies, through synthetic and real data.

Considering each LPP parameter (SD1, SD2, and SD12) and each lag 1, we calculated the median values among the 35 second windows, in the pre-yoga session and in the post-yoga session. For each subject, we obtained two median values of each LPP parameter and each lag corresponding to pre-yoga and post-yoga, respectively.

A paired Wilcoxon non-parametric statistical test was applied to all PRV parameters to study the differences between pre-yoga and post-yoga sessions. Analysis of temporal (SDNN, RMSSD, NN) and LLP parameters (SD1, SD2, SD12, for each lag) included 15 subjects, while analysis of spectral parameters ($P_{LFn}$ and $P_{HF}$) included 9 subjects. The difference can be considered to be significantly different from zero when p<0.05.

FIG. 14 shows an example of the NN interval series for pre- and post-yoga sessions, as well as their corresponding PSD. An overall increase in power is observed after the yoga session.

Temporal PRV parameters are shown in FIG. 15: there is an increase in NN (which translates to a decrease in the mean heart rate), SDNN and RMSSD, but it was only statistically significant in SDNN. Spectral PRV parameters are shown in FIG. 16: there is a decrease in $P_{LFn}$ and an increase in $P_{HF}$, but both are not significant in this case. The only LPP parameter which was found to be statistically different was the ratio SD12 (lags 5 and 7), shown in FIG. 16, showing a significant increase after yoga.

Several works have studied the role of yoga in the overall health and a healthy lifestyle. Also, yoga has been proposed for treatment of severe mental illnesses: it was found a reduction in general psychopathology ratings and an improvement in cognition and functioning in schizophrenic patients, and a significant benefit in reducing the severity of depressive symptoms. In those studies which focus on the autonomic function, they found an increase in parasympathetic activity, a decrease in sympathetic activity and an overall increase heart rate variability.

Our results agree with those found in the literature. While most temporal and spectral parameters did not show significant differences, possibly due to the small size of data, they indeed followed the same tendencies as other studies. We found an increase in NN (a decrease in mean heart rate) which was also observed in previous works. In most recordings, we found a tendency similar to the example shown in FIG. 14: in pre-yoga, the heart rate decreases over time as the yoga session approaches, while in post-yoga the heart rate increases over time. The increase in SDNN is related with an overall increase of total variability, while the increase in RMSSD is related to an increased parasympathetic activity.

Spectral parameters also show similar results. There is a decrease in LF power (in normalized units), an increase in HF power and a decrease in the LF/HF ratio, which translates to an increase in parasympathetic activity and a decrease in both sympathetic activity and sympathovagal tone. FIG. 14 also shows an increase in both LF and HF power, which may be related to the increased parasympathetic activity affecting both bands. Taking advantage of the capability of the NIVA band to estimate the respiratory rate, we found that it was located within the classic HF band (0.15 to 0.4 Hz) for all recordings, and no statistical differences were found in PHF when centering the HF band around respiratory rate compared to using the classic HF band. The main limitation for spectral analysis is that NIVA signal was very sensitive to movement artifacts, and only in 9 subjects we could find segments longer than 90 seconds with no outliers in the pulse interval series. We also repeated the statistical test for temporal parameters with only these 9 subjects, and the tendencies were the same, with SDNN being non-significant this time.

To overcome this limitation, we used other nonlinear parameters which can be computed in very short time windows, such as Lagged Poincare'Plot. Several previous studies reported the correlation between lagged SD1 and HF power, revealing its strong ability to detect increase in vagal modulation. According to recent literature, SD12 parameter relates to the nonlinear component of heartbeat dynamics (especially for l=5, 6) and an increase of sympathetic activity was found to decrease its value. Therefore, the increase in SD12 found in this work suggests a decrease in sympathetic activity. We also repeated this analysis using the whole recordings instead of the 35 second windows, and we found similar statistical differences in SD12 with lags 4 and 5.

In summary, we have shown that the NIVA band is able to detect changes in autonomic function after a yoga session. Similar to other heart rate variability studies, we have found that yoga increases parasympathetic activity and decreases the sympathovagal balance and the mean heart rate. There is also an overall increase in the total variability. To overcome the limitations found in the NIVA signal, which make difficult to analyze PRV parameters in the frequency domain, we used temporal and non-linear parameters, finding similar results than with spectral parameters.

While various example aspects and example embodiments have been disclosed herein, other aspects and embodiments will be apparent to those skilled in the art. The various example aspects and example embodiments disclosed herein are for purposes of illustration and are not intended to be limiting, with the true scope and spirit being indicated by the following claims.

What is claimed is:
1. A method comprising:
   (a) generating, via a piezoelectric sensor, a signal representing vibrations originating from a blood vessel of a subject, wherein the vibrations are indicative of heart beats or respirations of the subject;
   (b) obtaining a power spectral density of the signal;
   (c) determining a respiration rate of the subject by identifying a lowest frequency of the power spectral density at which a peak exceeding a predetermined power threshold exists;
   (d) using the respiration rate as a basis for selecting a portion of the signal;
   (e) determining a heart rate variability of the subject using the portion of the signal;
   (f) evaluating a parasympathetic nervous system response of the subject based on the heart rate variability;
   (g) administering a treatment protocol to the subject; and
   (h) repeating steps (a)-(f) to determine an efficacy of the treatment protocol.

2. The method of claim 1, wherein determining the heart rate variability comprises identifying consecutive heart rate peaks of the signal and determining durations between the consecutive heart rate peaks.

3. The method of claim 1, further comprising filtering the signal with a low pass filter to generate a filtered signal, wherein determining the heart rate variability comprises determining the heart rate variability using the filtered signal.

4. The method of claim 3, further comprising amplifying the filtered signal to generate an amplified signal, wherein determining the heart rate variability comprises determining the heart rate variability using the amplified signal.

5. The method of claim 4, further comprising filtering the amplified signal with a low-pass differentiator filter.

6. The method of claim 1, wherein the portion of the signal represents a first duration, the method further comprising:
   selecting a second portion of the signal that corresponds to a second duration that exceeds the first duration;
   determining a second heart rate variability based on the second portion of the signal; and
   evaluating a sympathetic nervous system response based on the second heart rate variability.

7. The method of claim 1, wherein generating the signal comprises generating the signal representing vibrations originating from a vein of a subject.

8. The method of claim 1, wherein the treatment protocol comprises one or more of oxytocin administration, narcotics administration, sedative administration, anxiolytics administration, behavioral therapeutic interventions, anxiolytics administration, behavioral therapeutic interventions, reiki, healing touch, meditation, yoga, exercise, sympathetic colitics administration, alpha and beta antagonists administration, environmental interventions, music therapy, art therapy, virtual reality therapy, or pet therapy.

9. The method of claim 1, further comprising using the heart rate variability to diagnose over-training in athletes, optimization of athletic performance, post-traumatic stress disorder, anxiety, pain, eating disorders, obesity, obesity surgery, autonomic dysfunction, depression, addiction to opiates, alcohol or other substances, delirium, acute or chronic illness, critical illness, post-surgical stress, traumatic brain injury, cancer, post-myocardial infarction, complications caused by local anesthesia or conscious sedation, burns, and/or complications of childbirth.

10. The method of claim 1, wherein the portion of the signal corresponds to heart beats that occur within a duration of time ranging from 2.5 seconds to 6 seconds.

11. A system comprising:
   one or more processors;
   a piezoelectric sensor; and
   a computer readable medium storing instructions that, when executed by the one or more processors, cause the system to perform functions comprising:
   (a) generating, via the piezoelectric sensor, a signal representing vibrations originating from a blood vessel of a subject, wherein the vibrations are indicative of heart beats or respirations of the subject;
   (b) obtaining a power spectral density of the signal;
   (c) determining a respiration rate of the subject by identifying a lowest frequency of the power spectral density at which a peak exceeding a predetermined power threshold exists;
   (d) using the respiration rate as a basis for selecting a portion of the signal;

(e) determining a heart rate variability of the subject using the portion of the signal;
(f) evaluating a parasympathetic nervous system response of the subject based on the heart rate variability;
(g) administering a treatment protocol to the subject; and
(h) repeating steps (a)-(f) to determine an efficacy of the treatment protocol.

12. The system of claim 11, comprising a master device that houses the one or more processors and the computer readable medium, and a slave device that houses the piezoelectric sensor.

13. The system of claim 11, wherein determining the heart rate variability comprises identifying consecutive heart rate peaks of the signal and determining durations between the consecutive heart rate peaks.

14. The system of claim 11, the functions further comprising filtering the signal with a low pass filter to generate a filtered signal, wherein determining the heart rate variability comprises determining the heart rate variability using the filtered signal.

15. The system of claim 14, the functions further comprising amplifying the filtered signal to generate an amplified signal, wherein determining the heart rate variability comprises determining the heart rate variability using the amplified signal.

16. The system of claim 15, the functions further comprising filtering the amplified signal with a low-pass differentiator filter.

17. The system of claim 11, wherein the portion of the signal represents a first duration, the functions further comprising:
selecting a second portion of the signal that corresponds to a second duration that exceeds the first duration;
determining a second heart rate variability based on the second portion of the signal; and
evaluating a sympathetic nervous system response based on the second heart rate variability.

18. The system of claim 11, further comprising filtering the signal with a low pass filter to generate a filtered signal, wherein determining the heart rate variability comprises determining the heart rate variability using the filtered signal.

19. A non-transitory computer readable medium storing instructions that, when executed by a system, cause the system to perform functions comprising:
(a) generating, via a piezoelectric sensor of the system, a signal representing vibrations originating from a blood vessel of a subject, wherein the vibrations are indicative of heart beats or respirations of the subject;
(b) obtaining a power spectral density of the signal;
(c) determining a respiration rate of the subject by identifying a lowest frequency of the power spectral density at which a peak exceeding a predetermined power threshold exists;
(d) using the respiration rate as a basis for selecting a portion of the signal;
(e) determining a heart rate variability of the subject using the portion of the signal;
(f) evaluating a parasympathetic nervous system response of the subject based on the heart rate variability;
(g) administering a treatment protocol to the subject; and
(h) repeating steps (a)-(f) to determine an efficacy of the treatment protocol.

20. The non-transitory computer readable medium of claim 19, wherein determining the heart rate variability comprises identifying consecutive heart rate peaks of the signal and determining durations between the consecutive heart rate peaks.

* * * * *